United States Patent [19]
Cerwin et al.

[11] Patent Number: 6,047,815
[45] Date of Patent: Apr. 11, 2000

[54] PACKAGE FOR SUTURES

[75] Inventors: Robert J. Cerwin, Pipersville, Pa.;
Martin Sobel, Flemington, N.J.;
Clifford A. Dey, Raritan, N.J.; Joseph Stanley Siernos, Whitehouse Station, N.J.; Marvin Alpern, Glen Ridge, N.J.;
Konstantin Ivanov, Bound Brook, N.J.

[73] Assignee: Ethicon, Inc.

[21] Appl. No.: 09/143,818

[22] Filed: Aug. 31, 1998

[51] Int. Cl.⁷ ............................................. A61B 17/06
[52] U.S. Cl. ......................... 206/63.3; 206/480; 206/225
[58] Field of Search ......................... 206/63.3, 225, 206/388, 478, 480, 482, 483, 408, 339, 380, 227, 381

[56] References Cited

U.S. PATENT DOCUMENTS

| | | |
|---|---|---|
| 4,424,898 | 1/1984 | Thyen et al. ........................... 206/63.3 |
| 4,887,710 | 12/1989 | Roshdy et al. .. |
| 4,961,498 | 10/1990 | Kalinski et al. .. |
| 4,967,902 | 11/1990 | Sobel et al. .. |
| 5,052,551 | 10/1991 | Cerwin et al. .. |
| 5,056,658 | 10/1991 | Sobel et al. .. |
| 5,099,994 | 3/1992 | Kalinski et al. .. |
| 5,131,533 | 7/1992 | Alpern . |
| 5,165,217 | 11/1992 | Sobel et al. .. |
| 5,179,818 | 1/1993 | Kalinski et al. .. |
| 5,180,053 | 1/1993 | Cascio et al. .. |
| 5,199,561 | 4/1993 | Roshdy et al. .. |
| 5,213,210 | 5/1993 | Cascio et al. .. |
| 5,230,424 | 7/1993 | Alpern et al. .. |
| 5,236,083 | 8/1993 | Sobel et al. .. |
| 5,271,495 | 12/1993 | Alpern . |
| 5,284,240 | 2/1994 | Alpern et al. .. |
| 5,487,469 | 1/1996 | Roshdy et al. .. |
| 5,529,175 | 6/1996 | Brunken . |
| 5,628,395 | 5/1997 | Daniele et al. .. |
| 5,655,652 | 8/1997 | Sobel et al. .. |
| 5,675,961 | 10/1997 | Cerwin et al. .. |

Primary Examiner—Paul T. Sewell
Assistant Examiner—Nhan T. Lam
Attorney, Agent, or Firm—Emil Richard Skula

[57] ABSTRACT

A package for sutures having a winding channel. The package has a base member and a cover member that is mounted to the base member. A plurality of cantilieverd doors cover the winding channel.

7 Claims, 7 Drawing Sheets

PACKAGE FOR SUTURES

TECHNICAL FIELD

The field of art to which this invention pertains is packaging, in particular, packages used for surgical sutures suitable for high-speed automatic packaging machinery.

BACKGROUND OF THE INVENTION

Packaging for surgical sutures and needles is well known in the art. The conventional packages serve several useful functions, including protecting the needles and sutures during handling, shipping, and storage. In addition, the packages facilitate access and release of the needles and sutures during surgery or other medical procedures prior to application. The packages may be used for surgical sutures armed with surgical needles or for unarmed surgical sutures without needles. There are two types of packages that have been conventionally used for surgical needles and sutures. One type of package is a paper folder package wherein a medical grade paperboard is folded and cut into a plurality of panels. The suture is then wound onto a panel and the package is assembled by folding the panels into a desired configuration, and then locking the panels in place using slits and locking tabs which have been cut into the panels. Another type of suture package which has been used is a tray package having a winding channel. These tray packages typically have an oval shape with outer and inner walls forming an oval winding channel. The packages are typically molded from plastics. The packages are mounted onto a winding fixture and sutures are then wound into the winding channel. Packages typically have a park member for mounting and securing a surgical needle if a surgical needle is mounted to the sutures. The park member can also be utilized for mounting one end of a suture wound into the winding channel. U.S. Pat. No. 4,961,498 discloses a two-piece suture package having an oval winding channel. U.S. Pat. No. 4,967,902 discloses a one-piece channel suture package having a plurality of door members which retain the suture in the channel. U.S. Pat. No. 5,230,424 discloses a package having a substantially square shape and having a square shaped suture channel wherein a plurality of cantilevered doors are mounted to an inner wall to maintain sutures in the channel. U.S. Pat. No. 5,665,652 discloses a package having an oval-shaped winding channel with a top friction plate member in lieu of doors or cantileevered doors. U.S. Pat. No. 5,131,533 discloses a needle park having a hinged section. U.S. Pat. No. 5,180,053 discloses a suture package having a cantilevered arm needle park.

Although the suture tray packages of the prior art are adequate and effective for their intended use, there is a need in this art for new suture tray packages having winding channels which are readily adaptable to high-speed packaging processes.

DISCLOSURE OF THE INVENTION

Therefore, it is an object of the present invention to provide a tray package having a winding channel which is useful in a high-speed packaging process for packaging surgical sutures.

Accordingly, a suture package is disclosed. The package has a base member having a top, a bottom and an outer periphery and a longitudinal axis. An outer wall extends upwardly from the periphery of said base member, said outer wall having an inner surface, an outer surface, and a top. A ledge member extends radially outward from the top of the outer wall; the ledge member has a top surface, a bottom surface and an outer periphery. An outer ledge wall extends upwardly from the periphery of the ledge member, said outer ledge wall has an inner surface, and outer surface and a top. A plurality of standoff members extend radially inward from the inner surface of the outer ledge wall onto at least part of the top surface of the ledge member. A plurality of rivet receiving holes extend through the base member. A flange member concentrically surrounds each rivet member; the flange member extends up from the top of the base member.

A castellated wall having a plurality of wall members separated by spaces extends upwardly from the top of the base member. The wall members and spaces define the castellated wall. The wall members each have an inner side, an outer side, opposed end sides and a top. The wall members are located interior to the outer wall and are spaced from the outer wall so as to form a winding track for receiving sutures, wherein the winding track consists of the top surface of the base member located between the outer surface of the castellated wall and the inner surface of the outer wall. There is an opening in the castellated wall for receiving sutures.

An annular recess surrounds each rivet hole on the bottom of the base member. A slit in the base member forms a hinged suture lifting tab, wherein said slit consists of a first slit substantially perpendicular to the longitudinal axis of the base member, said slit having first and second ends. A pair of opposed slits extend from said first and second ends, wherein said opposed slits have a first section which is substantially perpendicular to the first slit and a second section which is angulated inwardly from the first section. A pair of opposed, parallel first park walls extend up from the top surface of the base member, said walls having first and second ends and top surfaces and said walls substantially perpendicular to the longitudinal axis of the base member and parallel to the first slit. A second park wall extends up from the top of the base member, said wall being perpendicular to the first park walls and connecting the second ends of the first park walls. A wedge suture retaining member having a triangular shape extends from the top of each first park member adjacent to the second end of each member.

A suture channel cover member for mounting to the base member has a top, a bottom and an outer periphery. A plurality of rivet members extend downwardly from the bottom to the cover member. An inner track wall extends upwardly from the outer periphery of the cover member, said inner track wall has an inner side, an outer side and a top. A plurality of cantilevered cover door members extend radially outward from the top of the inner track wall, each door member has a top surface, a bottom surface, an inner end and an outer end. The door members have a notched opening in the outer end extending partially into each door member. The door members are separated by spaces. A rim member extends downwardly from the outer end of each door member. An opening in the inner track wall forms a suture exit port. A curved exit port arm is adjacent to the exit port, said port arm extends upwardly form the top surface of the base member from the track wall to a point on the base member interior to the track wall. A plurality of inner track spaces are located in the inner track wall, each said space being in substantial alignment with a space between a door member. A plurality of projection members extend radially outward from the outer surface of the inner track wall. An opening is located in the cover member forming a lifting tab window. A reinforcing guide member extends from the top of the cover member, said member having a first end, a second end and a top. A cantilevered clip arm consisting of a flat member having a top and a bottom, a first end, and a second end, wherein the first end of the clip arm is mounted to the second end of the reinforcing guide over a section of the tab window. The cover member is mounted to the base member to form the package of the present invention by aligning the cover member with the base member and inserting the rivets into the rivet receiving holes.

These and other features and advantages of the present invention will become more apparent from the following description and accompanying drawings.

DESCRIPTION OF THE PREFERRED EMBODIMENTS

Figure 1:
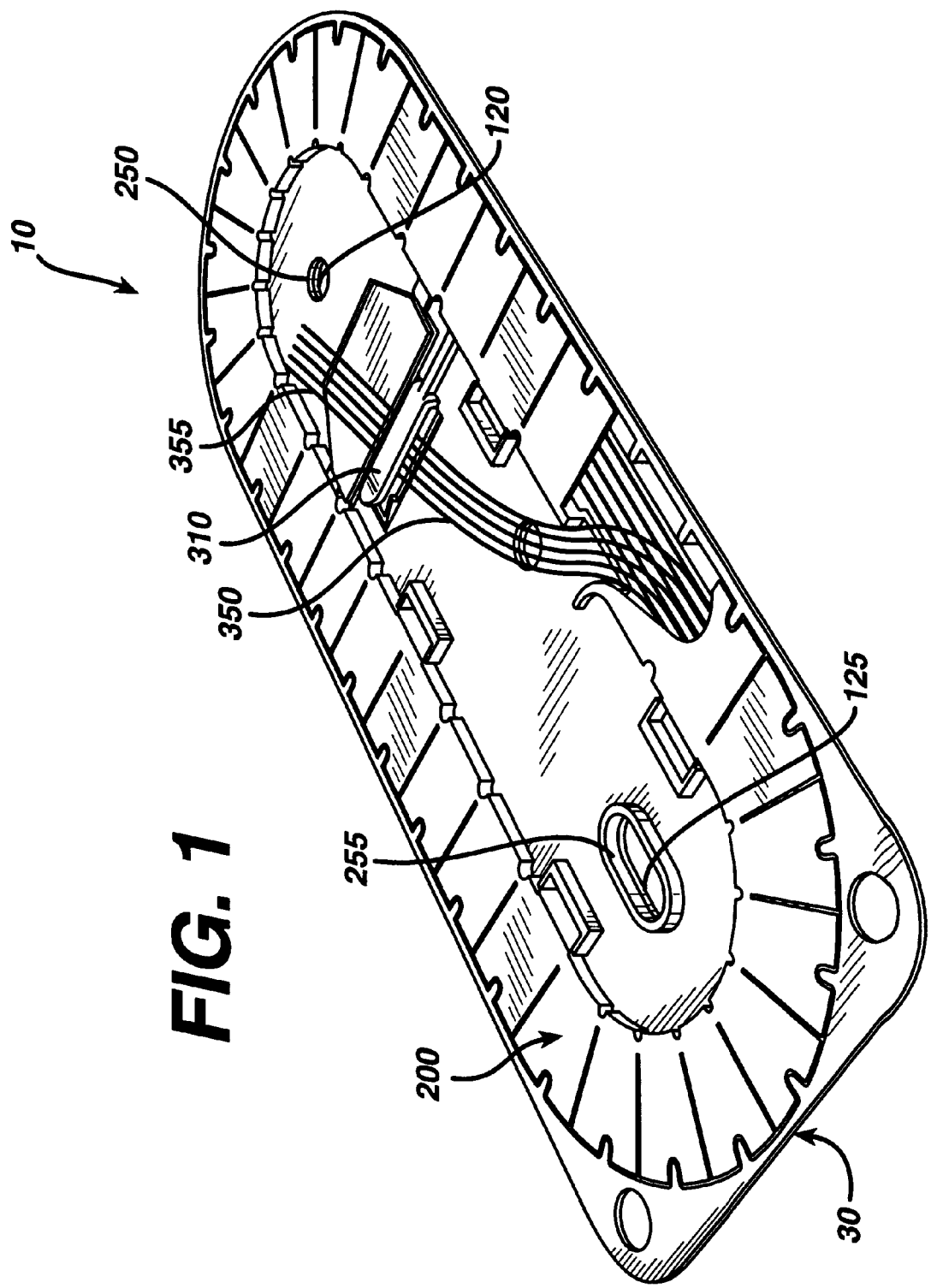
FIG. 1 is a perspective view of the package of the present invention having surgical sutures mounted therein.
Figure 5:
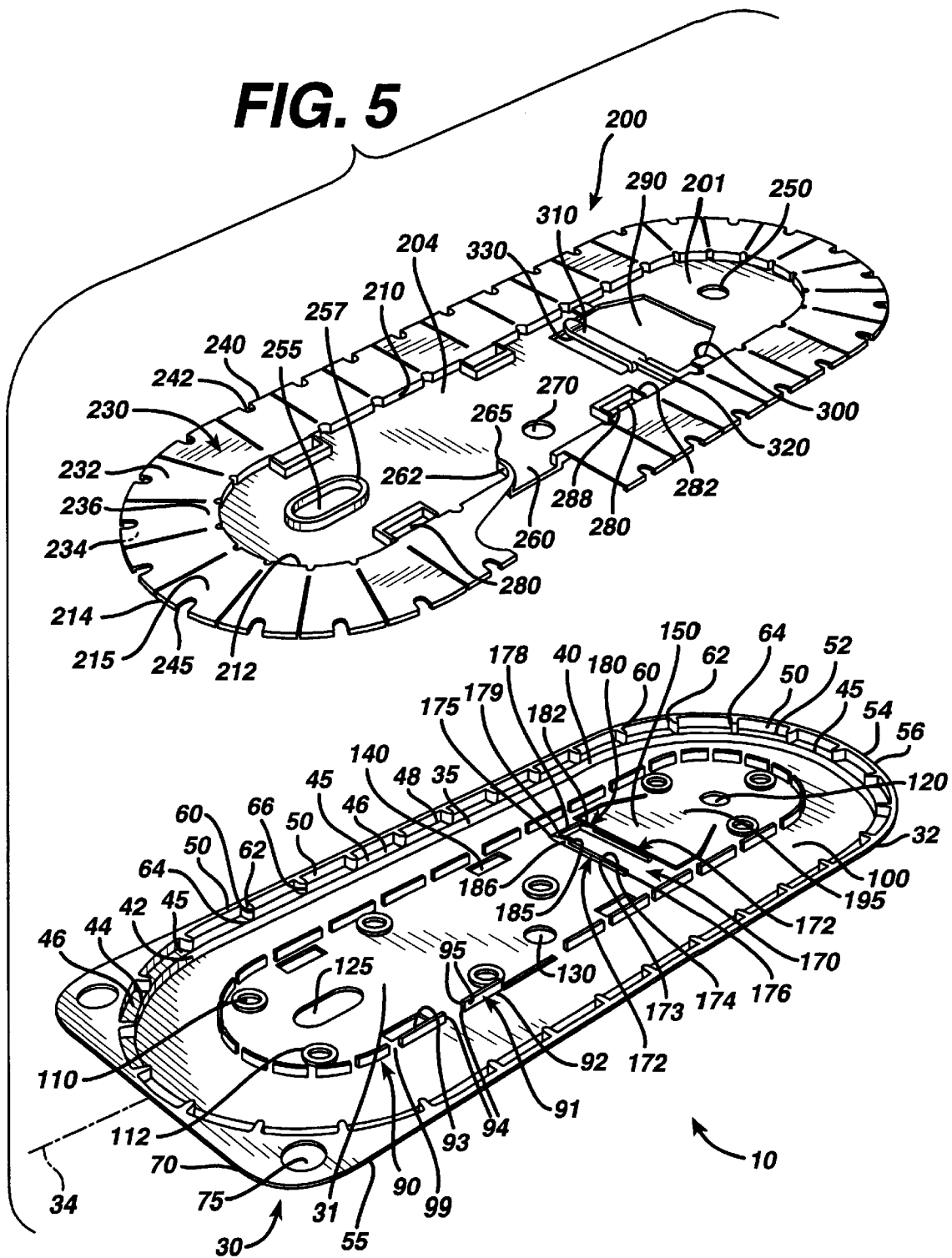
FIG. 5 is an exploded perspective view of the package of the present invention illustrating the base member and the suture channel cover member.

The package 10 of the present invention is illustrated in FIGS. 1–9. As seen in FIGS. 1 and 5, the package 10 has base member 30, suture channel cover member 200, and optional package cover 400. Referring now in more detail to FIGS. 1–6, the base member 30 is seen to have top 31 and bottom 32. Base member 30 is seen to have outer periphery 35. The base member is seen to be a substantially flat substantially oval shaped member having a longitudinal axis 34. However, although it is desired that the base member 30 along with the package 10 be oval shaped, other configurations can be used including circular, polygonal, square with rounded corners, and the like and combinations thereof and equivalents thereof. Extending upwardly about the periphery 35 of base member 30 is the outer wall 40. Outer wall 40 is seen to have inner side 42, outer side 43 and top 44. Extending radically outward from the top 44 of the outer wall 40 is the ledge 45. Ledge 45 is seen to have top 46, bottom 47, and periphery 48. Extending upwardly from the periphery 48 of the ledge 45 is the outer ledge wall 50. The ledge wall 50 is seen to have inner side 52, outer side 54, and top 56. The standoff members 60 are seen to extend from the top 46 of the ledge 45 and the inner side 52 of the outer ledge wall 50, or members 60 may simply extend out from inner side 52 over top side 46. Standoff members 60 are seen to have bottom 64 and flat tops 62. The standoff members 60 are seen to have a substantially cylindrically shaped cross-section with a curved surface 66. If desired, the standoff members 60 may have other configurations including rectangular, polygonal, oval, and triangular cross-sections, combinations thereof and equivalents thereof.

Figure 6:
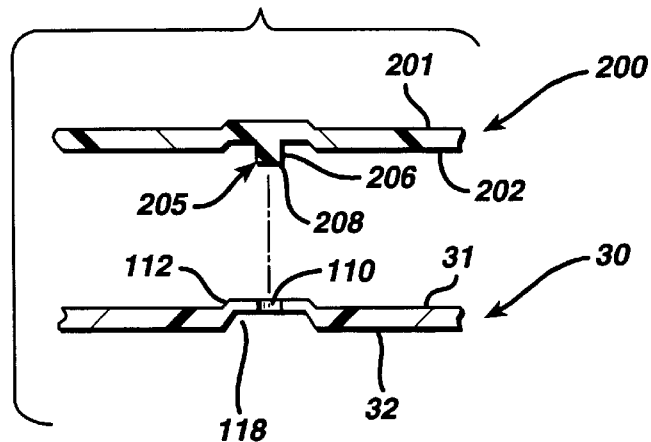
FIG. 6 is a partial cross-sectional view of the base member and the cover member illustrating the positioning of the rivets and rivet receiving holes prior to mounting.
Figure 7:
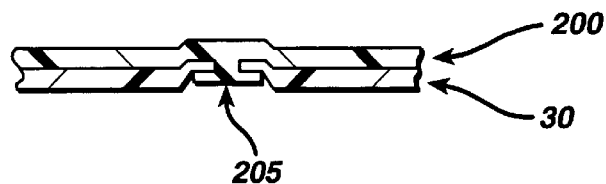
FIG. 7 is a partial cross-sectional view of the assembled package of the present invention after the rivets of the top cover member have been inserted in the rivet receiving holes of the base member and the ends of the rivets have been flattened.
Figure 8:
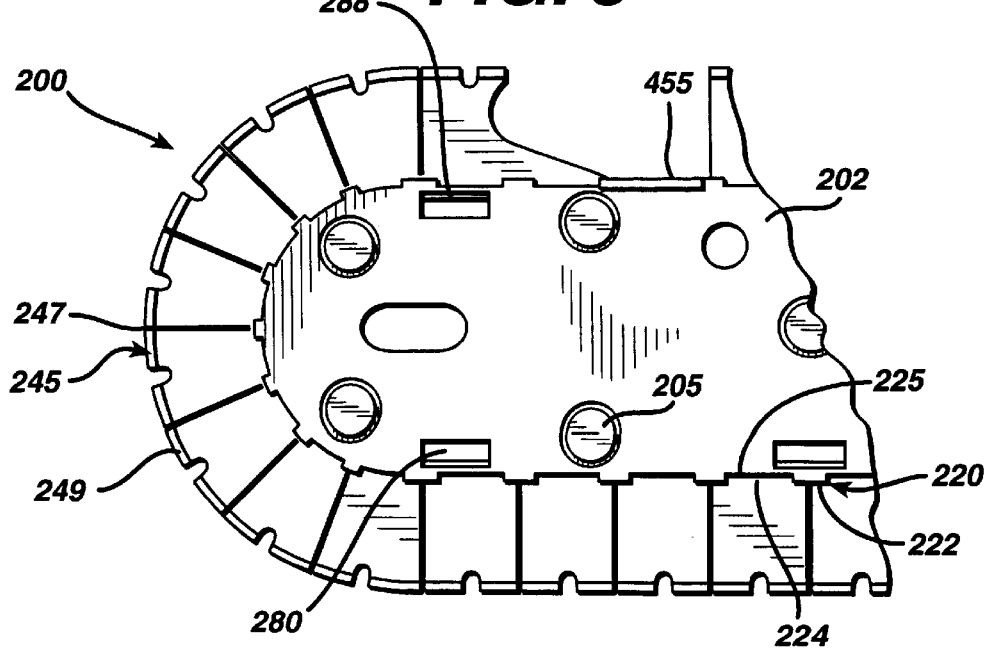
FIG. 8 is a partial bottom plan view of the suture channel cover member of a package of the present invention.
Figure 9:
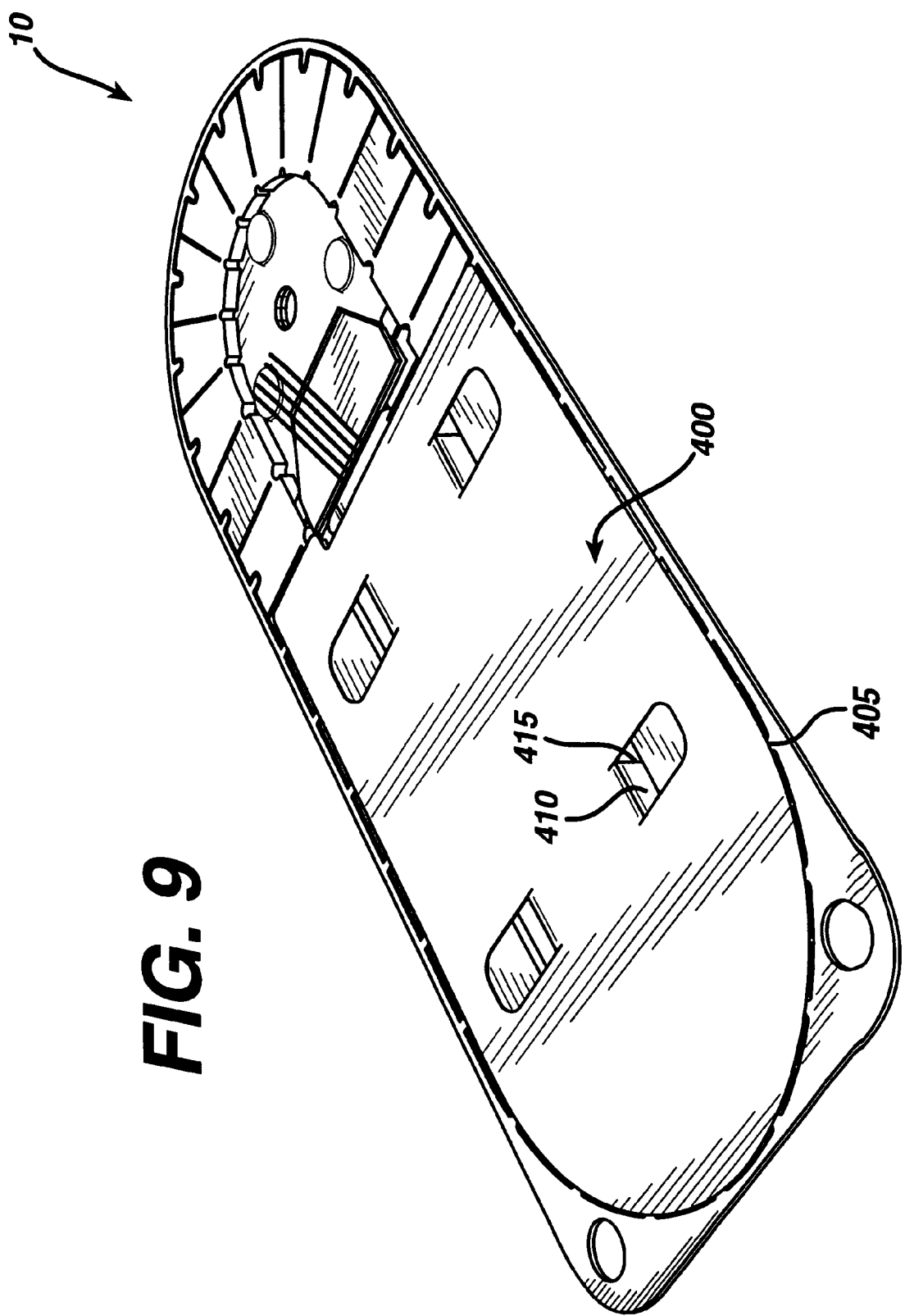
FIG. 9 is a perspective view of the package of the present invention after sutures have been loaded into the package and an optional protective cover has been attached.

Located interior to the outer wall 40 is the castellated wall 90. The castellated wall 90 is seen to have a substantially oval shape, and preferably has a shape similar to the shape of outer wall 40. The castellated wall 90 consists of a plurality of members 91 extending upward from the top 31 of the base member 30. Members 91 are seen to have bottoms 92, tops 93, ends 94, and sides 95. The castellated members 91 are seen to be separated by the openings 99. Extending through the bottom of the base member 30 interior to the castellated wall 90 are a plurality of rivet retention holes 110. The rivet retention holes 110 are seen to be circular holes extending through the base member 30. Each rivet hole 110 is surrounded by a circular flange member 112 extending up from the top 31 of the base member 30 concentrically about each hole 110. Referring to FIGS. 6–8, it can be seen that on the bottom 32 of the base member 30, each rivet retention hole 110 is surrounded by an annular space 118 to facilitate spreading of the bottom of a rivet.

Also extending through the base member 30, interior to the castellated wall 90, are the circular winding pin locating hole 120 and the oval pin locating hole 125. The holes 120 and 125 are seen to be disposed interior to castellated wall 90 and are at opposite ends of the base member. Also seen to extend through the base member 30 is the suture guiding locking hole 130. The cover cleat retention holes 140 are seen to extend through the base member 130 interior to the castellated wall 140. The holes are seen to be substantially rectangularly shaped, however, the holes may have any shape suitable for receiving cleats on paper cover 400. The suture lifting tab member 150 is seen to be located in base member 30 toward circular locating hole 120. The lifting tab 150 is seen to be formed in base member 30 by the slot 155. Slot 155 is seen to have slit 160 which is substantially perpendicular to the longitudinal axis 34 and has ends 161 and 162. Intersecting slot 60 on either end and perpendicular thereto are the side slots 164 and 165 having ends 166 and 167, respectively. Intersecting the ends 166 and 167 of side slots 164 and 165 are the angulated slots 168 and 169 having ends 190 and 191, respectively. Between the ends 190 and 191 of the angulated slots, is the living hinge member 195. Living hinge member 195 permits the lifting tab 150 to rotate about the hinge 195. An equivalent conventional hinge can be used in place of a living hinge, although not preferred. Adjacent to the slot 160 is the park receiving member 170. The park receiving member 170 is seen to have a pair of opposed parallel walls 172 having tops 174, ends 175 and 176 and sides 173. Connecting the members 172 and projecting up from the top 31 of base member 30 is the connecting member 179. Each side member 172 is seen to have on end 175 and extending upward from top 178 the ramp members 180. Ramp members 180 are substantially triangularly shaped having sloping surface 182 and top angular projection 185, and side wall 186 which is preferably perpendicular to top 174. If desired, base member 30 may have ear projections 70 extending radially outwardly from the top 56 of ledge wall 50. Ear projections 70 may have holes 75 extending therethrough. Also extending through base member 30 is the rectangular opening 450 for receiving suture port tab member 455.

Figure 2:
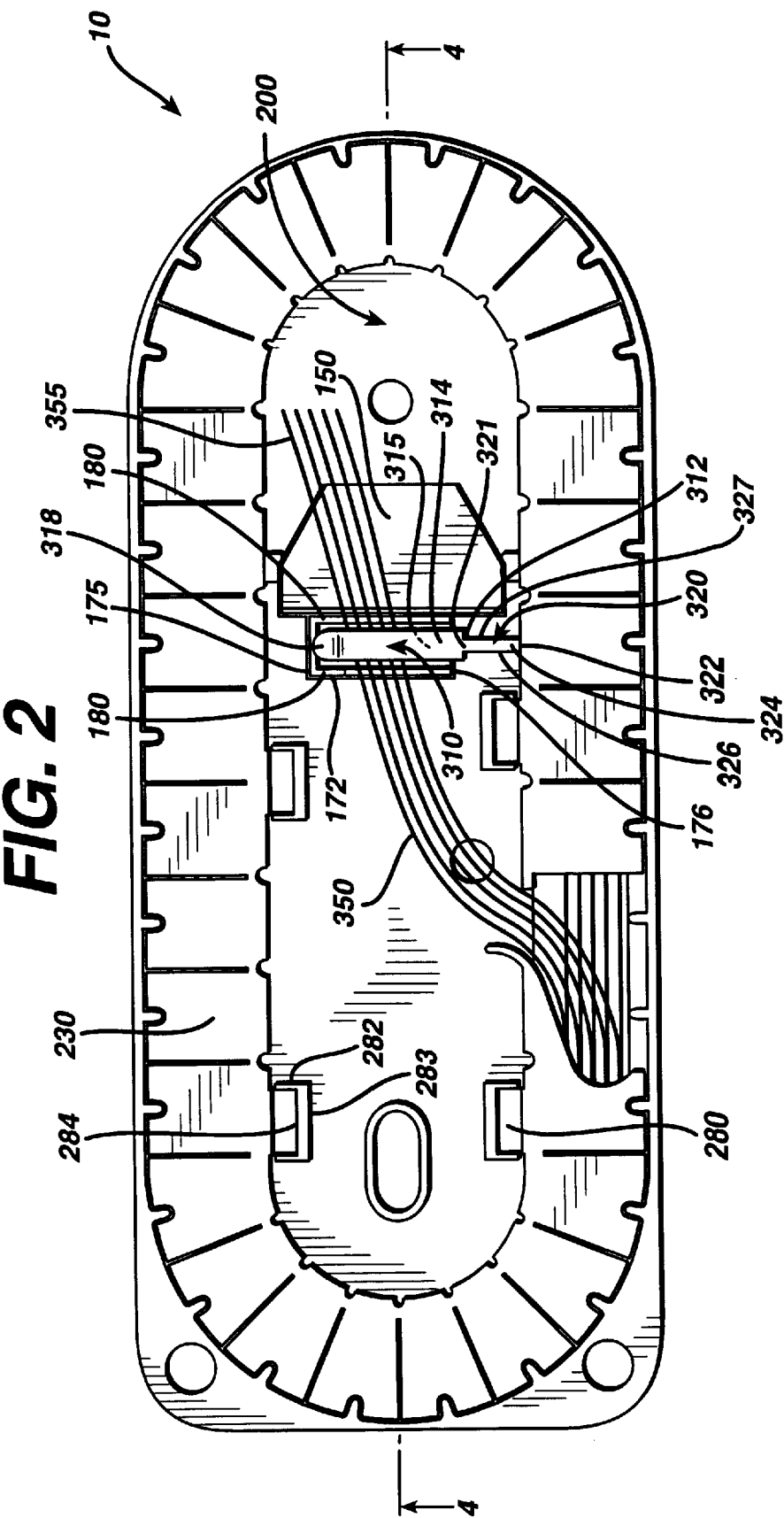
FIG. 2 is a top view of the package of the present invention of FIG. 1.
Figure 3:
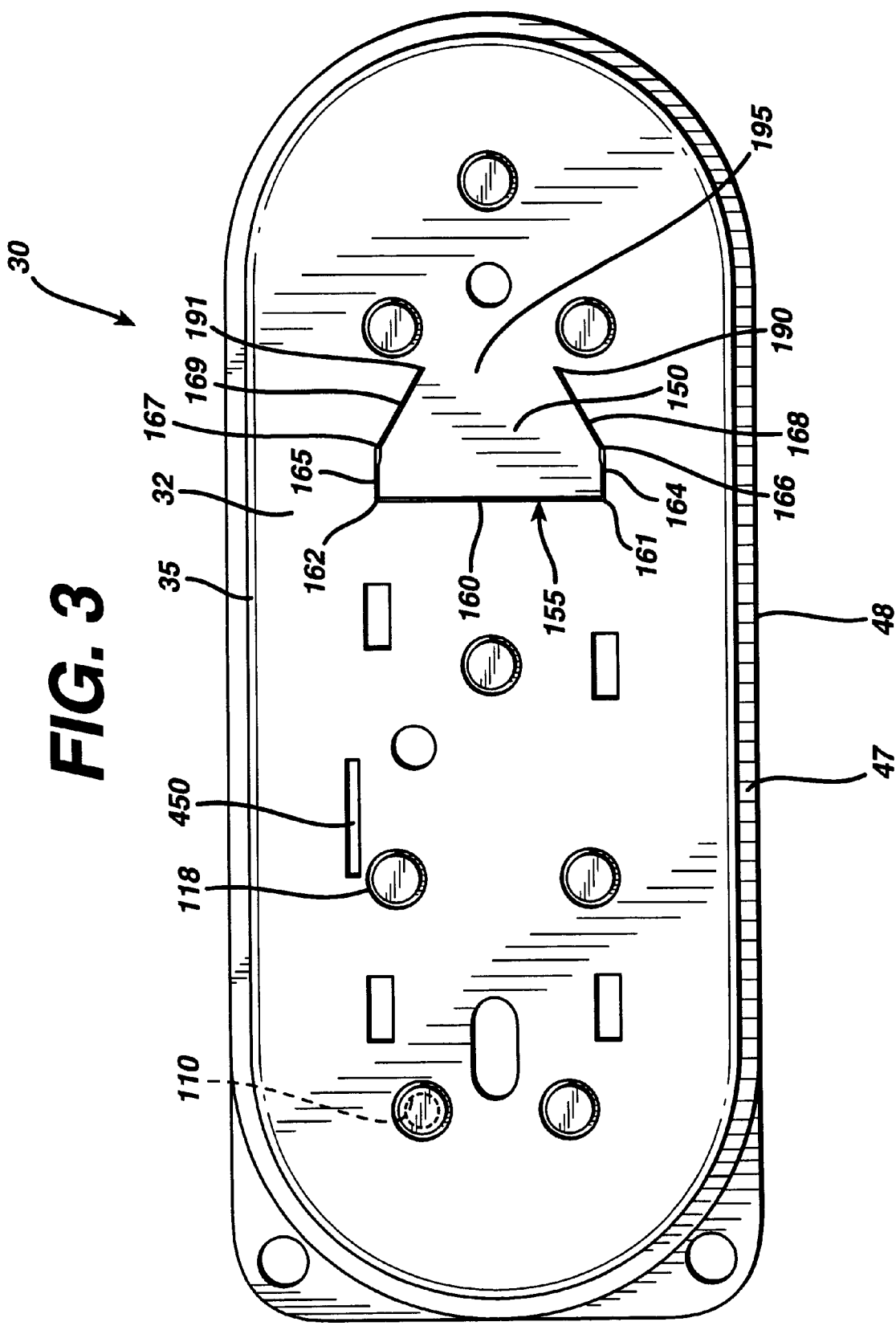
FIG. 3 is a bottom view of the package of FIG. 1.
Figure 4:
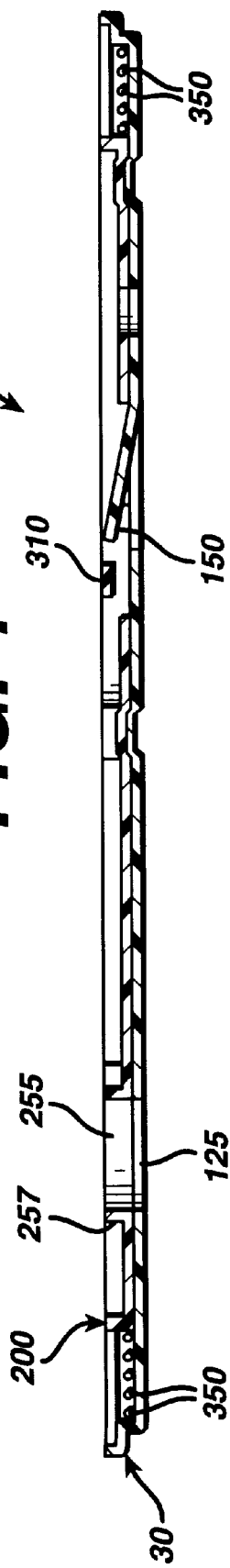
FIG. 4 is a longitudinal cross-sectional view of the package of FIG. 2 taken along view line 4—4.

Referring now to FIGS. 1, 2, and 5, the suture channel cover 200 is seen to be illustrated. The suture channel cover 200 has top 201, bottom 202, and periphery 204. Extending downwardly from the bottom 202 of the channel cover member 200 are the rivets 205 having sides 206 and bottoms 208. The rivets 205 are preferably circular in cross section, but may have other geometrical cross-sections including oval, square, polygonal, and the like and equivalents thereof. Extending upwardly from the top 201 of the cover 200 about the periphery 204 is the peripheral inner track wall 210. Inner track wall 210 is seen to have inner side 212, outer side 214, and top 215. Extending radially outward from the outer side 214 of track wall 210 are the stand-off projections 220. The projections 220 are seen to vary in size and to have either a square or a rectangular configuration. The projections 220 are seen to have outer surfaces 222. Between the projections 220 are the spaces 224. Also seen in inner side of the track wall 210 are the cavities 225. Cavities 225 are substantially rectangularly shaped or square shaped and are seen to be located in wall behind each stand-off projection 220.

Extending outwardly from the top 215 of the track wall 210 are the cantilevered cover members 230. The cover member 230 are seen to have tops 232, bottoms 234, and hinge ends 236. Each cover member is seen to be separated by a space 239. The cover members are further seen to have outer end 240, having central notch 242. The notches 242 are seen to be semi-circular in shape although other configurations can be used. Extending downward from the end 240 of cover member 230, is the downward rim 245. Downward rim 245 is seen to have sides 247 and bottom 249. The pin winding holes 250 and 255 are seen to be contained at opposite ends of the cover member 200. Winding pin hole 250 is seen to be circular in shape, while winding pin hole 255 is seen to be oval. However, other geometric shapes can be utilized. In addition, the rim member 257 is seen to extend up from the top 201 of suture channel cover 200 about the oval hole 255. The suture exit port 260 is seen to be contained in track wall 210. The curved arm 262 having end 265 is seen to extend from inner wall 210 interior to the inner wall 210. Extending downward from the bottom 202 of cover member 200 next to the port 260 is tab member 455. Adjacent to the suture exit port 260 is the circular winding pin locating hole 270. Extending through the cover member 200 are the cover tab mounting holes 280. Each tab hole is seen to have walls 282 and 283 and cleat member 288 extending inwardly from the inner surface 284 of wall 283. Contained in the cover member 200 is the lift tab window 290. Lift tab window 290 is seen to have locking posts 300 adjacent to either side of this opening and extending into the opening. Mounted over one end of the window 290 is the cantilevered clip arm 310. Cantilevered clip arm 310 is seen to extend from one end 321 of the reinforcing guide 320. Reinforcing guide 320 is seen to be substantially perpendicular to inner wall 210 and to have ends 321, 322, top 324, and sides 326 and 327. Clip arm 310 is seen to be a substantially flat rectangularly shaped member having hinge end 312 extending from the end 321 of the reinforcing guide 320, top 314, bottom 315, and curved end 318.

The packages 10 of the present invention are assembled in the following manner. Base member 30 is aligned with cover member 200 such that the rivets 205 are in alignment with the rivet receiving holes 110. Also, winding pin openings 255 and 250 are aligned with openings 125 and 120 respectively. Then, cover 200 is placed upon base member 30 such that the rivets 205 are inserted into and through the holes 110. When this is accomplished, the wall members 91 are contained within the spaces 224 between projections 220 and tab 455 is contained within opening 450. Then as seen in FIGS. 6, 7, and 8, the ends 208 of the rivets 205 are spread by using conventional techniques such as heating, ultrasonic treatments, and the like such that the cover 200 is firmly affixed to the base member 30, and the riveted or spread ends 208 are contained within annular openings 118. In order to mount sutures 350 in the package 10, the assembled package 10 is mounted into a conventional, rotatable winding fixture, such that the winding pins of the winding fixture are inserted through the winding pin openings 125 and 130 and 255 and 250 and a pin is inserted through suture guiding holes 130 and 270. One end 355 of a suture 350 is placed underneath the clip 310 such that the suture end 355 is resting on the top surfaces of the member 170. Then the suture is threaded through opening 260 into the channel 100 and guided into the channel 100 by a conventional stylus which lifts the cover door members 230 such that the suture is completely wound in the channel 100. This may be repeated with additional sutures 350. It can be seen that the member 180 prevents the end 355 of suture 350 from disengaging between the clip 310 and the members 170. Winding pins and suture locating pins are inserted through openings 125 and 255, 120 and 250, and 130 and 270 respectively. If desired, a cover member 400 may be applied to the package containing the wound suture. Cover member 400 is seen to have base member 405 and downwardly extending cleat members 410. Cleat members 410 are inserted through openings 280 and 140. The bottom 415 of the cleat member 410 is retained by the cleat retention member 288. The package 10 containing the sutures 350 may then be placed in a conventional pouch or package for conventional sterilization treatments such as gaseous sterilants, autoclaving, radiation and the like. When used by the physician, the package 10 is placed into a sterile field and the tab 150 is rotated upwardly through window 290 to present sutures 350 for removal. Tab 150 is locked in place by locking posts 300.

The packages of the present invention may be manufactured from conventional moldable materials. It is especially preferred to use polyolfin materials such as polyethylene, polypropylene and polyesters such as nylon, and equivalents thereof. Preferably the packages of the present invention may be injection molded, however, the packages may be formed by other conventional processes and equivalents thereof including thermos-forming. Sutures are mounted to the packages of the present invention preferably in the following manner:

Although this invention has been shown and described with respect to detailed embodiments thereof, it will be understood by those skilled in the art the various changes in form and detail thereof may be made without departing from the spirit and scope of the claimed invention.

We claim:

1. A package for surgical sutures, comprising:
   a base member having a top, a bottom and an outer periphery and a longitudinal axis;
   an outer wall extending upwardly from the periphery of said base member, said outer wall having an inner surface, an outer surface, and a top;
   a ledge member extending radially outward from the top of the outer wall, said ledge member having a top surface, a bottom surface and an outer periphery;
   an outer ledge wall extending upwardly from the periphery of the ledge member, said outer ledge wall having an inner surface, an outer surface and a top;
   a plurality of standoff members extending radially inward from the inner surface of the outer ledge wall onto at least part of the top surface of the ledge member;
   a plurality of rivet receiving holes extending through the base member;

a flange member concentrically surrounding each rivet member, said flange member extending up from the top of the base member;

a castellated wall comprising a plurality of wall members separated by spaces, said wall members and spaces defining said wall, said wall members each having an inner side, an outer side, opposed end sides and a top, said wall members extending up from the top of the base member, wherein said wall members are interior to the outer wall and spaced from the outer wall so as to form a winding track for receiving sutures;

a suture access opening in the castellated wall;

an annular recess surrounding each rivet hole on the bottom of the base member;

a slit in the base member forming a hinged suture lifting tab, wherein said slit comprises a first slit substantially perpendicular to the longitudinal axis of the base member, said slit having first and second ends, a pair of opposed slits extending from said first and second ends wherein said opposed slits have a first section which is substantially perpendicular to the first slit and a second section which is angulated inwardly from the first section, said slits forming the hinged tab;

a pair of opposed, parallel first park walls extending up from the top surface of the base member, said walls having first and second ends and top surfaces, said walls substantially parallel to the first slit;

a second park wall extending up from the top of the base member, said wall perpendicular to the first park walls and connecting the second ends;

a wedge member having a triangular shape extending from the top of each first park member adjacent to the second end of each member;

a suture channel cover member having a top, a bottom and an outer periphery;

a plurality of rivet members extending downwardly form the bottom to the cover member;

an inner track wall extending upwardly from the outer periphery of the cover member, said inner track wall having an inner side, an outer side and a top;

a plurality of cantilevered cover door members extending radially outward from the top of the inner track wall, each door member having a top surface, a bottom surface, an inner end and an outer end, said door members having a notched opening in the outer end extending partially into the door member, said door members separated by spaces;

a rim member extending downwardly from the outer end of each door member:

an opening in the inner track wall forming a suture exit port;

a curved exit port arm adjacent to the exit port, said port arm extending upwardly form the top surface of the base member from the track wall to a point on the base member interior to the track wall;

a plurality of inner track spaces in the inner track wall, each said space in substantial alignment with a space between a door member;

a plurality or projections extending radially outward from the exterior surface of the track wall;

an opening in the cover member forming a lifting tab window;

a reinforcing guide member extending from the top of the cover member, said member having a first end, a second end and a top;

a cantilevered clip arm comprising a flat member having a top and a bottom, a first end, and a second end, wherein the first end of the clip arm is mounted to the second end of the reinforcing guide, wherein the cover member is mounted to the base member such that the rivets are received by the rivet retention holes and the doors cover the winding track and the clip arm is centered between park walls and over at least part of the lifting tab window opening, and the lifting tab can be rotated upwardly at least partially into the window.

2. The package of claim 1 additionally comprising holes through the base member for receiving winding pins.

3. The package of claim 1 further comprising holes in the base member and holes in the cover member for receiving package cover cleats.

4. The package of claim 1 additionally comprising locking members extending upwardly from the top of the cover member on either side of the window, and partially extending into the window.

5. The package of claim 1 further comprising a cover, said cover comprising a flat member and mounting cleats extending downwardly form the cover.

6. The package of claim 5 further comprising a suture locating pin hole in both the base member and the cover member adjacent to the suture access port.

7. The package of claim 1 further comprising a suture wound into the winding channel.

* * * * *